(12) United States Patent
Haunert et al.

(10) Patent No.: US 7,449,609 B2
(45) Date of Patent: Nov. 11, 2008

(54) METHOD FOR PRODUCTION OF 1,6-HEXANEDIOL WITH A PURITY IN EXCESS OF 99.5%

(75) Inventors: Andrea Haunert, Mannheim (DE); Rolf Pinkos, Bad Dürkheim (DE); Thomas Krug, Worms (DE); Tilman Sirch, Schifferstadt (DE); Michael Koch, Mannheim (DE); Gerd-Dieter Tebben, Göttingen (DE)

(73) Assignee: BASF SE, Ludwigshafen (DE)

( * ) Notice: Subject to any disclaimer, the term of this patent is extended or adjusted under 35 U.S.C. 154(b) by 496 days.

(21) Appl. No.: 10/569,980

(22) PCT Filed: Jul. 7, 2005

(86) PCT No.: PCT/EP2005/007336

§ 371 (c)(1),
(2), (4) Date: Feb. 28, 2006

(87) PCT Pub. No.: WO2006/005504

PCT Pub. Date: Jan. 19, 2006

(65) Prior Publication Data

US 2008/0207958 A1    Aug. 28, 2008

(30) Foreign Application Priority Data

Jul. 9, 2004    (DE) .................. 10 2004 033 557

(51) Int. Cl.
    *C07C 29/149* (2006.01)
(52) U.S. Cl. .................................... 568/864
(58) Field of Classification Search .............. 568/864
    See application file for complete search history.

(56) References Cited

U.S. PATENT DOCUMENTS

| 5,981,769 | A | 11/1999 | Bauer et al. |
| 6,008,418 | A | 12/1999 | Bauer et al. |

FOREIGN PATENT DOCUMENTS

| DE | 196 07 954 A1 | 9/1997 |
| DE | 196 07 955 A1 | 9/1997 |
| WO | WO 97/31882 | 9/1997 |
| WO | WO 2004/046072 A1 | 9/1997 |
| WO | WO 2004/026798 A2 | 4/2004 |

OTHER PUBLICATIONS

Ullmann's Encyclopedia of Industrial Chemistry, 1989.

*Primary Examiner*—Elvis O Price
(74) *Attorney, Agent, or Firm*—Connolly Bove Lodge & Hutz LLP

(57) ABSTRACT

The present invention provides a process for preparing 1,6-hexanediol by hydrogenating dialkyl adipates, alkyl 6-hydroxycaproates, 1,4-cyclohexanedione and 4-hydroxycyclohexan-1-one as ester mixtures comprising impurities, by
a) freeing resulting the esterification mixture of excess alcohol and low boilers in a first distillation stage (alcohol removal),
b) carrying out a separation of the bottom product in a second distillation stage into an ester fraction substantially free of 1,4-cyclohexanediols and a fraction comprising at least the majority of the 1,4-cyclohexanediols,
c) catalytically hydrogenating the ester fraction substantially free of 1,4-cyclohexanediols (ester hydrogenation) and
d) in a purifying distillation stage, obtaining 1,6-hexanediol from the hydrogenation effluent in a manner known per se, which comprises selectively hydrogenating the ester mixture before stage a) and/or before stage b) (purifying hydrogenation).

20 Claims, 1 Drawing Sheet

METHOD FOR PRODUCTION OF 1,6-HEXANEDIOL WITH A PURITY IN EXCESS OF 99.5%

Figure 1:
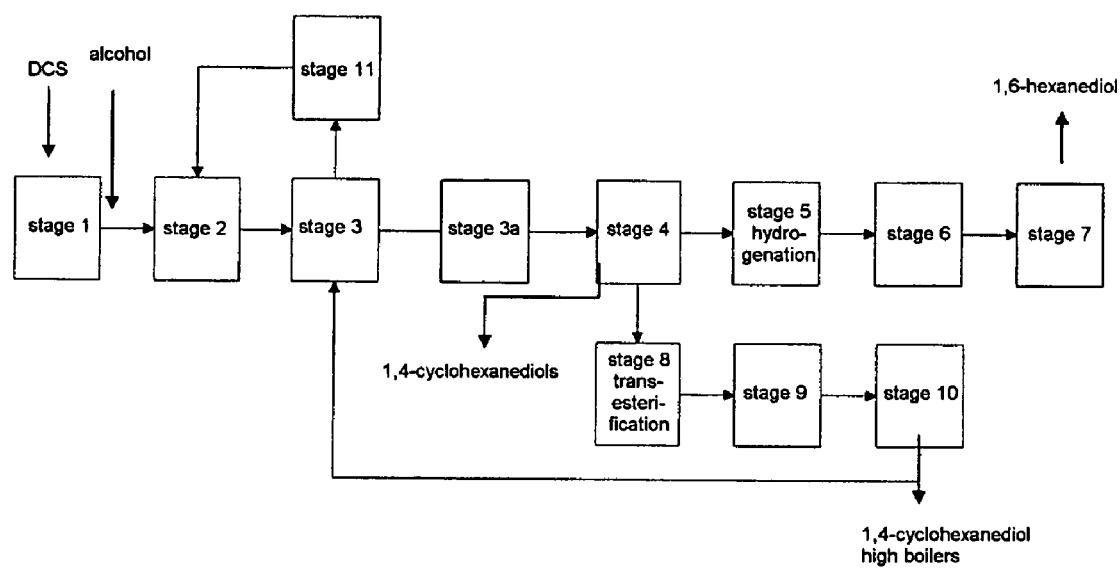

This application is a National Stage application of PCT/EP05/007336 filed Jul. 7, 2005, claiming the benefit of German application DE 10 2004 033 557.5, filed Jul. 9, 2004.

DESCRIPTION

The invention relates to a process for preparing 1,6-hexanediol in a purity of >99.5% from mixtures comprising dialkyl adipates, alkyl 6-hydroxycaproates, 1,4-cyclohexanedione and 4-hydroxycyclohexan-1-one.

1,6-Hexanediol constitutes a sought-after monomeric building block which is used predominantly in the polyester and polyurethane sector. In these applications, 1,4-cyclohexanediol in the 1,6-hexanediol is undesired.

Suitable processes for preparing 1,6-hexanediol are described in DE-A 196 07 954 and DE-A 196 07 955. In these processes, dicarboxylic acid solution (DCS) is esterified initially with a $C_1$-$C_{10}$-alkanol and the resulting esterification mixture, after removal of excess alcohol and other low boilers, is separated by distillation. An ester fraction is obtained which is substantially free of 1,4-cyclohexanediols.

From this ester fraction, 1,6-hexanediol with a purity of at least 99% is prepared by final hydrogenation (ester hydrogenation).

Even though the $C_6$ ester mixture prepared by this process is substantially free of 1,4-cyclohexanediols, 1,4-cyclohexanediols are found in the hydrogenation effluent depending on the quality of the dicarboxylic acid solution used and cannot be removed fully by distillation and therefore appear at 0.05-0.5% in the pure 1,6-hexanediol.

Reactants for the processes, described in DE-A 196 07 954 and DE-A 196 07 955, for the preparation of 1,6-hexanediol are the aqueous solutions of carboxylic acids which are formed as by-products in the oxidation of cyclohexane to cyclohexanol and cyclohexanone (cf. Ullmann's Encyclopedia of Industrial Chemistry, 5th Ed., 1987, Vol. A8, p. 49), referred to hereinbelow as dicarboxylic acid solution (DCS). These dicarboxylic acid solutions contain (calculated without water in % by weight) generally between 10 and 40% adipic acid, between 10 and 40% 6-hydroxycaproic acid, between 1 and 10% glutaric acid, between 1 and 10% 5-hydroxyvaleric acid, between 1 and 5% 1,2-cyclohexanediols, between 1 and 5% 1,4-cyclohexanediols, between 2 and 10% formic acid and a multitude of further mono- and dicarboxylic acids, esters, oxo and oxa compounds whose individual contents generally do not exceed 5%. Examples include acetic acid, propionic acid, butyric acid, valeric acid, caproic acid, oxalic acid, malonic acid, succinic acid, 4-hydroxybutyric acid and γ-butyrolactone.

A more precise analysis of the dicarboxylic acid solution revealed 1,4-cyclohexanedione and 4-hydroxycyclohexan-1-one as further ingredients at from 0.01 to 2% by weight.

Both substances are removed only insufficiently after esterification and distillative purification of the esters. 1,4-Cyclohexanedione and 4-hydroxycyclohexanone which get into the final hydrogenation of the ester mixture to hexanediol (ester hydrogenation) are hydrogenated there under the conditions of the ester hydrogenation to 1,4-cyclohexanediol and lead to a contamination which can be removed only with high yield losses of the hexanediol product.

It is therefore an object of the present invention to provide a simple and inexpensive process which affords 1,6-hexanediol in purer form from 1,4-cyclohexanedione- and 4-hydroxycyclohexan-1-one-containing dicarboxylic acid solution without the yield of 1,6-hexanediol falling.

It has now been found that, surprisingly, this object is achieved when the ester mixture is subjected to a hydrogenation before a distillation.

The present invention provides a process for preparing 1,6-hexanediol with a purity of >99% by hydrogenating dialkyl adipates, alkyl 6-hydroxycaproates and 1,4-cyclohexanedione and 4-hydroxycyclohexan-1-one as ester mixtures comprising impurities, by a) freeing the resulting esterification mixture of excess alcohol and low boilers in a first distillation stage ("alcohol removal" hereinbelow), b) carrying out a separation of the bottom product in a second distillation stage into an ester fraction substantially free of 1,4-cyclohexanediols and a fraction comprising at least the majority of the 1,4-cyclohexanediols, c) catalytically hydrogenating the ester fraction substantially free of 1,4-cyclohexanediols ("ester hydrogenation" hereinbelow) and d) in a purifying distillation stage, obtaining 1,6-hexanediol from the hydrogenation effluent in a manner known per se, which comprises selectively hydrogenating the ester mixture before stage a) and/or before stage b), but preferably before stage b), of the distillation for the 1,4-cyclohexanediol removal ("purifying hydrogenation" hereinbelow).

During the inventive selective purifying hydrogenation of the 1,4-cyclohexanedione and 4-hydroxycyclohexan-1-one present in the ester mixture, the adipic acid and alkyl 6-hydroxycaproates which are likewise present are not hydrogenated to alcohols. This prevents them from being lost as bottom product in the distillation (stage b)) which preferably follows the purifying hydrogenation and the hexanediol yield from falling drastically.

Surprisingly, the amount found of 1,4-cyclohexanediols which cannot be removed 1,6-hexanediol is distinctly reduced or no longer present at all after the hydrogenation, without the 1,6-cyclohexanediol yield having fallen.

Dialkyl adipates to be used in accordance with the invention are in particular esters of adipic acid with low molecular weight alcohols, for example with alcohols having from 1 to 4 carbon atoms, or ester mixtures comprising them, include reactants of any origin which, owing to their preparation method, comprise 1,4-cyclohexanediol and 4-hydroxycyclohexan-1-one as impurities.

Preference is given to using for the process according to the invention an ester mixture as obtained by esterifying a dicarboxylic acid mixture which comprises adipic acid, 6-hydroxycaproic acid, 1,4-cyclohexanediols, 1,4-cyclohexanedione and 4-hydroxycyclohexan-1-one and which is obtained as a by-product of the oxidation of cyclohexane to cyclohexanone/cyclohexanol with oxygen or oxygen-containing gases by extraction of the reaction mixture with water, with a low molecular weight alcohol, preferably n- or isobutanol, more preferably methanol (ester fraction a)).

The preparation of the dicarboxylic acid mixture, the ester fraction (referred to above as steps a) and b)) and the process for preparing 1,6-hexanediol (steps c) and d)) is known and described in detail in DE-A 196 07 954 A and DE-A 196 07 955. The entire contents of these documents are therefore incorporated by reference into the present application.

Particular preference is given to using a mixture in the purifying hydrogenation which is obtained by removing the excess esterification alcohol and/or low boilers in a first distillation stage (alcohol removal). Low boilers refer to by-products which have a lower boiling point than the desired esters, especially 1,2-cyclohexanediols, valerolactone, methyl 5-hydroxyvalerate, dimethyl glutarate, dimethyl succinate. The alcohol removal is known as stage 3 from DE-A 196 07 955 and DE-A 196 07 954, which are explicitly incorporated by reference.

The ester mixture obtained after the purifying hydrogenation is divided by separation in a further distillation stage (stage b) of the process according to the invention), which is known per se and is described, for example, as stage 4 in DE-A 196 07 954, into an ester fraction substantially free of 1,4-cyclohexanediols and a fraction comprising at least the majority of the 1,4-cyclohexanediols. The ester fraction which is substantially free of 1,4-cyclohexanediols is hydrogenated to the hexanediol.

The purifying hydrogenation may be carried out in the process according to the invention and in the processes disclosed in DE-A 196 07 954 and DE-A 196 07 955 directly after the esterification, i.e. before the alcohol removal or after the alcohol removal, more preferably after the alcohol removal.

The purifying hydrogenation is effected at from 20 to 300° C, preferably from 50 to 200° C, more preferably from 100 to 160° C, and at a hydrogen pressure of from 1 to 200 bar, preferably from 1 to 100 bar of $H_2$, more preferably at from 10 to 50 bar of $H_2$, with fixed bed, suspended catalyst or homogeneous catalysts.

The catalysts used for the purifying hydrogenation in the process according to the invention are preferably heterogeneous catalysts which contain at least one metal of group 8 to 12 of the Periodic Table, for example ruthenium, osmium, iridium, platinum, palladium, rhodium, iron, copper, cobalt, nickel and zinc, and combinations of these metals. These metals may be used either in the form of the pure metals or of the compounds thereof, for example oxides or sulfides. Preference is given to using copper, nickel, cobalt, ruthenium or palladium catalysts. These catalysts may be applied to the customary supports, for example $TiO_2$, $Al_2O_3$, $ZrO_2$, $SiO_2$, carbon or mixtures thereof. The thus obtained supported catalysts may be present in all known finishing forms. Examples are extrudates or tablets.

Preference is given to the use of supported palladium-, ruthenium- and/or copper-containing catalysts.

Suitable for use in the process of the present invention are Raney copper, Raney nickel and Raney cobalt catalysts. These Raney catalysts may be present in all known finishing forms, for example as tablets, extrudates or granules. Suitable Raney copper catalysts are, for example, the Raney copper catalysts in the form of nuggets which are disclosed by WO 99/03801, which is explicitly incorporated herein by reference. These catalysts have a particle size of the nuggets of from 2 to 7 mm, a copper content of from 40 to 90% by weight, a Langmuir surface area of from 5 to 50 $m^2/g$, a copper surface area of from 0.5 to 7 $m^2/g$, an Hg pore volume of from 0.01 to 0.12 ml/g and an average pore diameter of from 50 to 300 nm.

Also particularly suitable for use in the process according to the invention is a catalyst which comprises ruthenium supported on shaped titanium dioxide bodies, the shaped titanium dioxide bodies being obtained by treating commercial titanium dioxide, before or after the shaping, with from 0.1 to 30% by weight of an acid in which titanium dioxide is sparingly soluble, and which is used in the process according to the invention. Ruthenium may be used either in the form of the pure metal or in the form of a compound thereof, for example oxide or sulfide.

The catalytically active ruthenium is applied by processes known per se, preferably to prefabricated $TiO_2$ as the support material.

A titanium dioxide support suitable with preference for use in the ruthenium-containing catalyst may be obtained in accordance with DE 197 38 464 by treating commercial titanium dioxide, before or after the shaping, with from 0.1 to 30% by weight of an acid, based on titanium dioxide, in which the titanium dioxide is sparingly soluble. Preference is given to using titanium dioxide in the anatase modification. Examples of such suitable acids are formic acid, phosphoric acid, nitric acid, acetic acid or stearic acid.

The ruthenium active component may be applied in the form of a ruthenium salt solution to the thus obtained titanium dioxide support in one or more impregnation stages. Subsequently, the impregnated support is dried and, if appropriate, calcined. However, it is also possible to precipitate ruthenium from a ruthenium salt solution, preferably with sodium carbonate, onto titanium oxide present as a powder in aqueous suspension. The precipitated solids are washed, dried, calcined if appropriate and shaped. In addition, it is also possible to convert volatile ruthenium compounds, for example ruthenium acetylacetonate or ruthenium carbonyl, into the gas phase and apply them to the support in a manner known per se (chemical vapor deposition).

The thus obtained, supported catalysts may be present in all known finishing forms. Examples are extrudates, tablets or granules. Before they are used, the ruthenium catalyst precursors are reduced by treating with hydrogenous gas, preferably at temperatures above 100° C. Preference is given to passivating the catalysts before they are used in the process according to the invention with oxygenous gas mixtures, preferably with air-nitrogen mixtures, at temperatures of from 0 to 50° C., preferably at room temperature. It is also possible to install the catalyst in the hydrogenation reactor in oxidic form and to reduce it under reaction conditions.

The catalyst which is particularly preferred in accordance with the invention has a ruthenium content of from 0.1 to 10% by weight, preferably from 2 to 6% by weight, based on the total weight of the catalyst composed of catalytically active metal and support. The inventive catalyst may have a sulfur content of from 0.01 to 1% by weight, based on the total weight of the catalyst (sulfur determination: coulometric).

The ruthenium surface area is from 1 to 20 $m^2/g$, preferably from 5 to 15 $m^2/g$, and the BET surface area (determined to DIN 66 131) is from 5 to 500 $m^2/g$, preferably from 50 to 200 $m^2/g$.

The inventive catalysts have a pore volume of from 0.1 to 1 ml/g. The catalysts also feature a cutting hardness of from 1 to 100 N.

If the activity and/or selectivity of the catalyst sink in the course of operation, the catalyst used in accordance with the invention may be regenerated by measures known to those skilled in the art. These preferably include a reductive treatment of the catalyst in a hydrogen stream at elevated temperature. If appropriate, the reductive treatment may be preceded by an oxidative treatment. In this treatment, the catalyst bed is flowed through at elevated temperature with a molecular oxygen-containing gas mixture, for example air. There is also the possibility of washing the catalyst with a suitable solvent, for example ethanol or THF, and subsequently drying it in a gas stream.

The hydrogenation may also be effected by literature hydrogenation reagents such as $NaBH_4$, $LiAlH_4$, etc., at from 20 to 200° C., preferably from 50 to 200° C., more preferably from 100 to 160° C. The hydrogenation may be carried out continuously and batchwise, preferably continuously.

The subsequent workup of the ester mixture obtained after the purifying hydrogenation is effected as described in DE-A 196 07 954 A and DE-A 196 07 955 for the ester stream which has not been subjected to any purifying hydrogenation.

The hydrogenation of the esters (ester hydrogenation) to hexanediol is effected in a manner known per se as described in DE-A 196 07 954, in particular at from 20 to 300° C. and at a pressure of from 1 to 50 bar (in the case of hydrogenations in the gas phase over a fixed bed catalyst) or at a pressure in the range of from 30 to 350 bar (in the case of hydrogenations in the liquid phase with fixed bed or suspended catalyst). The hydrogenation may be carried out batchwise, preferably continuously.

The hydrogenation effluent of the ester hydrogenation consists substantially of 1,6-hexanediol and the esterification alcohol. Further constituents are 1,5-pentanediol, 1,4-butanediol, 1,2-cyclohexanediols and small amounts of monoalcohols having from 1 to 6 carbon atoms and water.

The hydrogenation effluent of the ester hydrogenation is fed in the next stage into, for example, a membrane system or preferably a distillation column and separated into the esterification alcohol which additionally comprises the majority of the further low-boiling components and a stream which predominantly 1,6-hexanediol as well as 1,5-pentanediol. At a pressure of from 10 to 1500 mbar, preferably from 30 to 1200 mbar, more preferably from 50 to 1000 mbar, top temperatures of from 0 to 120° C., preferably from 20 to 100° C., more preferably from 30 to 90° C., and bottom temperatures of from 100 to 270° C., preferably from 140 to 260° C., more preferably from 160 to 250° C, are attained.

The 1,6-hexanediol-containing stream is purified in a column. In this purification, 1,5-pentanediol, the 1,2-cyclohexanediols and any further low boilers present are removed overhead. When the 1,2-cyclohexanediols and/or 1,5-pentanediol are to be obtained as additional products of value, they may be separated in a further column. Any high boilers present are discharged via the bottom.

1,6-Hexanediol is withdrawn from a sidestream of the column in a purity of >99.5% with a distinctly reduced 1,4-cyclohexanediol content of from 0.005 to 0.1% by weight.

At pressures of from 1 to 1000 bar, preferably from 5 to 800 mbar, more preferably from 20 to 500 mbar, top temperatures of from 50 to 200° C., preferably from 60 to 150° C., and bottom temperatures of from 130 to 270° C., preferably from 150 to 250° C., are attained.

When only relatively small amounts of 1,6-hexanediol are to be prepared, the stages may also be combined in a batchwise fractional distillation.

The process according to the invention thus constitutes a simple and inexpensive procedure for obtaining highly pure 1,6-hexanediol with minimal amounts of 1,4-cyclohexanediols.

The examples which follow serve to illustrate the invention without restricting it.

EXAMPLE 1

Batchwise Purifying Hydrogenation

Example 1a 0.15 kg of ester mixture (approx. 90% by weight of dimethyl adipate and 10% by weight of methyl hydroxycaproate) which contained about 1500 ppm of 1,4-cyclohexanedione was reacted with 10 g of a Pd/Al$_2$O$_3$ catalyst at 130° C. and 30 bar of hydrogen for 180 min. The effluent contained approx. 10% by weight of methyl hydroxycaproate, approx. 90% by weight of dimethyl adipate, 380 ppm of 1,4-cyclohexanediol, 200 ppm of 1,4-cyclohexanedione and 1050 ppm of 4-hydroxycyclohexanone.

Example 1b 0.15 kg of ester mixture (approx. 90% by weight of dimethyl adipate and 10% by weight of methyl hydroxycaproate) which contained about 1500 ppm of 1,4-cyclohexanedione was reacted with 10 g of a 2% Ru/Al$_2$O$_3$ catalyst at 130° C. and 30 bar of hydrogen for 180 min. The effluent contained approx. 10% by weight of methyl hydroxycaproate, approx. 90% by weight of dimethyl adipate, 1490 ppm of 1,4-cyclohexanediol, 0 ppm of 1,4-cyclohexanedione and 0 ppm of 4-hydroxycyclohexanone.

Example 1c 0.15 kg of ester mixture (approx. 90% by weight of dimethyl adipate and 10% by weight of methyl hydroxycaproate) which contained about 1500 ppm of 1,4-cyclohexanedione was reacted with 10 g of a 5% Ru/SiO$_2$ catalyst at 130° C. and 30 bar of hydrogen for 150 min. The effluent contained approx. 10% by weight of methyl hydroxycaproate, approx. 90% by weight of dimethyl adipate, 1720 ppm of 1,4-cyclohexanediol, 0 ppm of 1,4-cyclohexanedione and 0 ppm of 4-hydroxycyclohexanone.

Example 1d 0.15 kg of ester mixture (approx. 90% by weight of dimethyl adipate and 10% by weight of methyl hydroxycaproate) which contained about 1500 ppm of 1,4-cyclohexanedione was reacted with 10 g of a 5% Ru/TiO$_2$ catalyst at 130° C. and 30 bar of hydrogen for 150 min. The effluent contained approx. 10% by weight of methyl hydroxycaproate, approx. 90% by weight of dimethyl adipate, 1560 ppm of 1,4-cyclohexanediol, 0 ppm of 1,4-cyclohexanedione and 0 ppm of 4-hydroxycyclohexanone.

Example 1e 0.15 kg of ester mixture (approx. 90% by weight of dimethyl adipate and 10% by weight of methyl hydroxycaproate) which contained about 1500 ppm of 1,4-cyclohexanedione was reacted with 10 g of a 2% Ru/C catalyst at 130° C. and 30 bar of hydrogen for 150 min. The effluent contained approx. 10% by weight of methyl hydroxycaproate, approx. 90% by weight of dimethyl adipate, 1800 ppm of 1,4-cyclohexanediol, 0 ppm of 1,4-cyclohexanedione and 0 ppm of 4-hydroxycyclohexanone.

Example 1f 0.15 kg of ester mixture (approx. 90% by weight of dimethyl adipate and 10% by weight of methyl hydroxycaproate) which contained about 1500 ppm of 1,4-cyclohexanedione was reacted with 10 g of a 2% Ru/αAl$_2$O$_3$ catalyst at 130° C. and 30 bar of hydrogen for 180 min. The effluent contained approx. 10% by weight of methyl hydroxycaproate, approx. 90% by weight of dimethyl adipate, 2400 ppm of 1,4-cyclohexanediol, 0 ppm of 1,4-cyclohexanedione and 0 ppm of 4-hydroxycyclohexanone.

Example 1e 0.15 kg of ester mixture prepared according to DE-A 196 07 954 (after stage a); (approx. 5% by weight of dimethyl adipate and 16% by weight of methyl hydroxycaproate) which contained about 0.07% by weight of 1,4-cyclohexanedione and 0.4% by weight of 4-hydroxycyclohexanone was reacted with 10 g of a 5% Ru/TiO$_2$ catalyst at 150° C. and 30 bar of hydrogen for 150 min. The effluent contained approx. 16% by weight of methyl hydroxycaproate, approx. 25% dimethyl adipate, 0 ppm of 1,4-cyclohexanedione and 0 ppm of 4-hydroxycyclohexanone.

EXAMPLE 2

Continuous Hydrogenation, Before Stage b)

A C$_6$ ester mixture prepared according to DE-A 196 07 954 (after alcohol and low boiler removal before stage b); (approx. 25% by weight of dimethyl adipate and 16% by weight of methyl hydroxycaproate) which contained about 0.07% by weight of 1,4-cyclohexanedione and 0.4% by weight of 4-hydroxycyclohexanone was converted continuously in a fixed bed reactor over a 2% Ru/TiO$_2$ catalyst which had been activated beforehand in a hydrogen stream at 180° C. Hydrogenation conditions: trickle bed, 250 ml of catalyst, 1.5 mm extrudates, feed 750-1500 g/h, no circulation, 30 bar, 150° C.). The effluent contained approx. 16% methyl hydroxycaproate, approx. 25% by weight of dimethyl adipate, <20 ppm of 1,4-cyclohexanedione and 0 ppm of 4-hydroxycyclohexanone.

EXAMPLE 3

Preparation of 1,6-hexanediol (See FIG. 1)

Stage 1: (Dewatering)

0.1 kg of dicarboxylic acid solution (adipic acid approx. 17% by weight, approx. 13% by weight of 6-hydroxycaproic acid, approx. 1.5% by weight of 1,4-cyclohexanediols, approx. 0.08% by weight of 1,4 cyclohexanedione, approx. 45% water) was distilled continuously in a distillation apparatus (three-tray bubble-cap tray column with external oil heating circuit, oil temperature 150° C, tray volume each approx. 25 ml, feed via the bubble-cap trays) with attached randomly packed column (approx. 4 theoretical plates, no reflux at the top). The top product obtained was 0.045 kg with a formic acid content in water of approx. 3%. In the bottom stream (5.5 kg), the water content was approx. 0.4%.

Stage 2: (Esterification)

5.5 kg of the bottom stream from stage 1 were reacted with 8.3 kg of methanol and 14 g of sulfuric acid. The acid number of the effluent minus sulfuric acid was approx. 10 mg KOH/g.

Stage 3: (Alcohol Removal)

In a column, the esterification stream from stage 2 was distilled (1015 mbar, top temperature 65° C. up to bottom temperature 125° C.). 7.0 kg were drawn off via the top. 6.8 kg were obtained as the bottom product.

Stage 3a:

The bottom product from stage 3 was converted continuously in a fixed bed reactor over a 2% Ru/TiO$_2$ catalyst which had been activated beforehand in a hydrogen stream at 180° C. (Hydrogenation conditions: trickle bed, 250 ml of catalyst, 1.5 mm extrudates, feed 750 g/h, no circulation, 30 bar, 150° C.). The effluent contained approx. 16% methyl hydroxycaproate, approx. 25% dimethyl adipate, <20 ppm of 1,4-cyclohexanedione and 0 ppm of 4-hydroxycyclohexanone.

Stage 4: (1,4-cyclohexanediol Removal)

In a 50 cm randomly packed column, the stream from stage 3a was fractionally distilled (1 mbar, top temperature from 70 to 90° C. up to bottom temperature 180° C.). The 1,4-cyclohexanediols were obtained in the bottoms.

0.6 kg was distilled off as low boilers (1,2-cyclohexanediols, valerolactone, methyl 5-hydroxyvalerate, dimethyl glutarate, dimethyl succinate, inter alia); 4.3 kg were obtained as the fraction comprising predominantly dimethyl adipate and methyl 6-hydroxycaproate.

Stage 5: (Continuous Hydrogenation, Substream)

2.7 kg of C$_6$ ester mixture from stage 4 were hydrogenated continuously in a 25 ml reactor over a catalyst (catalyst, 60% CuO, 30% Al$_2$O$_3$, 10% Mn$_2$O$_3$) which had been activated beforehand in a hydrogen stream at 180° C. Hydrogenation conditions: feed 20 g/h, no circulation, 220 bar, 220° C.). The ester conversion was 99.5%, the 1,6-hexanediol selectivity was above 99%. Approx. 150 to 250 ppm of 1,4-cyclohexanediols are found in the hydrogenation effluent.

Stage 6 and 7: (Hexanediol Purification)

2.5 kg of the hydrogenation effluent from stage 5 were fractionally distilled (distillation still having attached 70 cm randomly packed column, reflux ratio 2). At 1013 mbar, 0.5 kg of methanol was distilled off and, after application of reduced pressure (20 mbar in stage 7), predominantly the 1,2-cyclohexanediols and 1,5-pentanediol distilled off. Afterward (b.p. 146° C.), 1,6-hexanediol distilled off with a purity of >99.7%. The main by-product is approx. 200-300 ppm of 1,4-cyclohexanediol.

Stage 8:

2.9 kg of the bottom effluent from stage 4 were admixed with 3.8 kg of methanol and 3.8 g of tetraisopropyl titanate and converted continuously in a 1 m-long tubular reactor of capacity 440 ml which was filled with 3 mm V2A rings. The average residence time was approx. 2 h.

Stage 9:

The effluent from stage 8 was fractionally distilled analogously to the apparatus described in stage 3. At top temperature 65° C., 3.5 kg were distilled off (predominantly methanol). 2.2 kg remained in the bottoms.

Stage 10:

The bottoms from stage 9 were fractionally distilled analogously to stage 4 up to a bottom temperature of 160° C. 1.3 kg were obtained as distillate and can be hydrogenated directly or recycled into the 4$^{th}$ stage. (Composition: 52% by weight of methyl 6-hydroxycaproate, 31% by weight of dimethyl adipate, 5% by weight of dimethyl glutarate, 4% by weight of methyl 5-hydroxycaproate and a multitude of further, quantitatively insignificant components).

Stage 11:

7 kg of the top product of stage 3 were fractionally distilled at 1015 mbar on a 20 cm randomly packed column. 0.8 kg of first runnings were obtained at top temperature from 59 to 65° C. and comprised, in addition to predominantly methanol, C$_1$-C$_4$-monoethyl esters. At top temperature 65° C., 5.6 kg of methanol were obtained in a purity of >99.5%. The bottoms (0.6 kg) consisted predominantly of water.

What is claimed is:

1. A process for preparing 1,6-hexanediol comprising hydrogenating dialkyl adipates, alkyl 6-hydroxycaproates and 1,4-cyclohexanedione and 4-hydroxycyclohexan-1-one as ester mixtures comprising impurities, the process further comprising:
   a) freeing the resulting esterification mixture of excess alcohol and low boilers in a first distillation stage;
   b) carrying out a separation of the bottom product in a second distillation stage into an ester fraction substantially free of 1,4-cyclohexanediols and a fraction comprising at least the majority of the 1,4-cyclohexanediols;
   c) catalytically hydrogenating the ester fraction substantially free of 1,4-cyclohexanediols; and
   d) in a purifying distillation stage, obtaining 1,6-hexanediol from the hydrogenation effluent in a manner known per se, which comprises selectively hydrogenating the ester mixture before stage a) and/or before stage b) (purifying hydrogenation).

2. The process according to claim 1, wherein the purifying hydrogenation is carried out over a heterogeneous catalyst.

3. The process according to claim 1, wherein the purifying hydrogenation is carried out at from 20 to 300° C. and from 1 to 200 bar of $H_2$.

4. The process according to claim 1, wherein the purifying hydrogenation is carried out over supported palladium-, ruthenium- and/or copper-containing catalysts.

5. The process according to claim 1, wherein the purifying hydrogenation is carried out over ruthenium supported on shaped titanium dioxide bodies.

6. The process according to claim 1, wherein the reactant used is an ester mixture as obtained
   a) by esterifying with a low molecular weight alcohol a dicarboxylic acid mixture which comprises adipic acid, 6-hydroxycaproic acid and small amounts of 1,4-cyclohexanediols and which is obtained as a by-product in the oxidation of cyclohexane to cyclohexanone/cyclohexanol with oxygen or oxygen-containing gases and by water extraction of the reaction mixture (ester fraction a)).

7. The process according to claim 1, wherein the reactant used is an ester mixture in which excess alcohol and low boilers have been removed from ester fraction a) (ester fraction b)).

8. The process according to claim 2, wherein the purifying hydrogenation is carried out at from 20 to 300° C. and from 1 to 200 bar of $H_2$.

9. The process according to claim 2, wherein the purifying hydrogenation is carried out over supported palladium-, ruthenium- and/or copper-containing catalysts.

10. The process according to claim 3, wherein the purifying hydrogenation is carried out over supported palladium-, ruthenium- and/or copper-containing catalysts.

11. The process according to claim 2, wherein the purifying hydrogenation is carried out over ruthenium supported on shaped titanium dioxide bodies.

12. The process according to claim 3, wherein the purifying hydrogenation is carried out over ruthenium supported on shaped titanium dioxide bodies.

13. The process according to claim 4, wherein the purifying hydrogenation is carried out over ruthenium supported on shaped titanium dioxide bodies.

14. The process according to claim 2, wherein the reactant used is an ester mixture as obtained
   a) by esterifying with a low molecular weight alcohol a dicarboxylic acid mixture which comprises adipic acid, 6-hydroxycaproic acid and small amounts of 1,4-cyclohexanediols and which is obtained as a by-product in the oxidation of cyclohexane to cyclohexanone/cyclohexanol with oxygen or oxygen-containing gases and by water extraction of the reaction mixture (ester fraction a)).

15. The process according to claim 3, wherein the reactant used is an ester mixture as obtained
   a) by esterifying with a low molecular weight alcohol a dicarboxylic acid mixture which comprises adipic acid, 6-hydroxycaproic acid and small amounts of 1,4-cyclohexanediols and which is obtained as a by-product in the oxidation of cyclohexane to cyclohexanone/cyclohexanol with oxygen or oxygen-containing gases and by water extraction of the reaction mixture (ester fraction a)).

16. The process according to claim 4, wherein the reactant used is an ester mixture as obtained a) by esterifying with a low molecular weight alcohol a dicarboxylic acid mixture which comprises adipic acid, 6-hydroxycaproic acid and small amounts of 1,4-cyclohexanediols and which is obtained as a by-product in the oxidation of cyclohexane to cyclohexanone/cyclohexanol with oxygen or oxygen-containing gases and by water extraction of the reaction mixture (ester fraction a)).

17. The process according to claim 5, wherein the reactant used is an ester mixture as obtained
   a) by esterifying with a low molecular weight alcohol a dicarboxylic acid mixture which comprises adipic acid, 6-hydroxycaproic acid and small amounts of 1,4-cyclohexanediols and which is obtained as a by-product in the oxidation of cyclohexane to cyclohexanone/cyclohexanol with oxygen or oxygen-containing gases and by water extraction of the reaction mixture (ester fraction a)).

18. The process according to claim 2, wherein the reactant used is an ester mixture in which excess alcohol and low boilers have been removed from ester fraction a) (ester fraction b)).

19. The process according to claim 3, wherein the reactant used is an ester mixture in which excess alcohol and low boilers have been removed from ester fraction a) (ester fraction b)).

20. The process according to claim 4, wherein the reactant used is an ester mixture in which excess alcohol and low boilers have been removed from ester fraction a) (ester fraction b)).

* * * * *